United States Patent [19]

Krauling et al.

[11] Patent Number: 5,166,072
[45] Date of Patent: Nov. 24, 1992

[54] APPARATUS FOR THE CULTIVATION OF IMMOBILIZED MICRO-ORGANISMS

[75] Inventors: Jörg Krauling, Cologne; Hans-Jürgen Henzler, Solingen; Imre Pascik, Monheim; Claus Müller, Kuerten; Jörg Baumgarten, Wuppertal; Alois Molitor, Leverkusen, all of Fed. Rep. of Germany

[73] Assignee: Bayer Aktiengesellschaft, Leverkusen, Fed. Rep. of Germany

[21] Appl. No.: 403,015

[22] Filed: Sep. 5, 1989

Related U.S. Application Data

[63] Continuation of Ser. No. 58,478, Jun. 5, 1987, abandoned.

[30] Foreign Application Priority Data

Jun. 26, 1986 [DE] Fed. Rep. of Germany ....... 3621328

[51] Int. Cl.$^5$ .............................................. C12M 1/40
[52] U.S. Cl. .................................... 435/288; 435/311; 435/313; 435/813; 422/140; 422/147; 210/151
[58] Field of Search ................................... 422/140–143, 422/139, 140, 143, 147, 231; 435/288, 313, 818, 310, 311, 315, 316, 813; 210/150, 151; 261/122, 124, 42

[56] References Cited

U.S. PATENT DOCUMENTS

| | | | |
|---|---|---|---|
| 2,865,816 | 12/1958 | Stefanye et al. | 435/300 |
| 3,142,542 | 7/1964 | Schwartzenbek et al. | 422/143 |
| 3,542,523 | 11/1970 | Wall | 422/143 |
| 4,443,551 | 4/1984 | Lionetti et al. | 422/143 |
| 4,545,909 | 10/1985 | Atkinson et al. | 435/285 |
| 4,673,552 | 6/1987 | Li et al. | 422/143 |
| 4,764,347 | 8/1988 | Milligan | 422/113 |
| 5,041,216 | 8/1991 | Henzler et al. | 210/151 |

FOREIGN PATENT DOCUMENTS 0145647  6/1985  European Pat. Off. .
0001141  of 1916  United Kingdom .
0009989  of 1916  United Kingdom .

Primary Examiner—Robert J. Warden
Assistant Examiner—William H. Beisner
Attorney, Agent, or Firm—Sprung Horn Kramer & Woods

[57] ABSTRACT

An apparatus for cultivating immobilized micro-organisms consisting of a fluidized bed reactor with fittings for gassing and a retainer system for the immobilized biocatalysts. The fluidized bed reactor is characterized in that the fittings for gassing consist of several segments with gas outlets arranged on the base of the fluidized bed reactor, which admit gas alternately or cyclically. A central gas outflow opening, pointing upwards, can be provided in the fluidized bed reactor as a further gassing unit. The method of operating the fluidized bed is characterized in that circulating gassing occurs in the reactor by means of sequential opening of the gas inflow openings of the segment-shaped fittings. In addition, switches may occur from the central gassing unit to gassing by means of the segment-shaped fittings or vice-versa.

8 Claims, 3 Drawing Sheets

APPARATUS FOR THE CULTIVATION OF IMMOBILIZED MICRO-ORGANISMS

This application is a continuation of application Ser. No. 058,478, filed Jun. 5, 1987, now abandoned.

BACKGROUND OF THE INVENTION

The invention relates to a fluidized bed reactor for the cultivation of immobilised biocatalysts suspended in effluent with fittings for gassing and a retainer system for the immobilised biocatalysts. Also, the invention relates to a process for the operation of the fluidized bed reactor.

Increasingly, micro-organisms or enzymes are bound to special carriers in the cleaning of effluent and in enzymatic reactions, in order to achieve a heightened activity of the biocatalysts. Fixed bed and fluidized bed reactors are used as reactors. In fixed beds, the biocatalysts are often only partly utilized because of uneven packing or because of an uneven growth of the organisms. The process can also be disadvantageously influenced (e.g. through changes in pH) by concentration gradients in the fixed bed. Accordingly it is better, in many processes, to use a fluidized bed reactor in which a sufficient mixing of the fluid phase occurs, so that the carriers are in a suspended state or can be temporarily fluidized.

The energy for fluidizing can be either introduced via the fluid phase (by pump recirculation) or by gassing the fluid-solid mixture. The gas-operated fluidized bed is an especially useful reactor type for aerobic fermentation processes. A reduction of the energy introduced for fluidizing the biocatalysts is made possible by building in guides, such as e.g. baffle plates or guide tubes. In large installations, the fluctuating movements that often arise in gas-operative fluidized beds give rise to serious oscillations in the fittings which has often lead to the destruction of the guides or their anchorages.

In continuous processes, there is a further problem in the retention of the often expensive biocatalysts in the reactor. The customary method of retention by filtration is in many cases not practicable, as the filters block up and/or only low filtrate flow rates are achieved, which in turn necessitate large filter surfaces, thus causing high costs.

SUMMARY OF THE INVENTION

The object of the invention is to improve the cultivation of immobilised, suspended biocatalysts in a fluidized bed reactor by improved gassing, taking economic aspects (low investment and running costs) into account.

According to the invention this object is achieved for a fluidized bed reactor with fittings for gassing and an integrated retainer system for the immobilised biocatalysts in that the fittings for gassing consist of several segments arranged on the base of the fluidized bed reactor with gas outflow openings to which gas is applied alternately or in rotation.

It is advantageous to provide a central gas outflow opening directed upwards as a further built-in unit for gassing.

In order to avoid blockages, the gas outflow openings of the gas distributor incline towards the ground at an angle of $\beta = 30°$ to $90°$ from the horizontal. The distance between the gas outflow openings is 0.0 to 1 m and the opening angle $\alpha$ of the segments is $30°$ to $180°$, preferably $60°$ to $120°$. The number of segments can vary between 2 and 12, and their radial extension can vary between $r = D/10$ and $D/2$, preferably between $D/5$ and $D/2$ ($D$ = reactor diameter). The diameter of the central gassing unit should be 5% to 10% of the reactor diameter $D$. It is advantageous for several individual segments to be combined into one gassing unit.

Whether gassing takes place through a single gassing segment or through the central gassing unit, a marked circulation current develops, leading to fluidizing of the solids for significantly lower gas throughputs (roughly only 70 to 90% compared to the usual surface gassing). If in the case of gassing with one segment, the gas throughputs is increased until the gas velocity is so high that complete suspension is achieved, it is surprisingly found that the solids are first fluidized opposite the point of gassing, then at those points lying at a right-angle to the location of gassing and only finally in the neighbourhood of the point of gassing.

As a result of this fact, an improved gassing possibility emerges, which consists in having the segments receive gas one after the other in the direction of the circumference (circulating gassing). Significantly lower gas throughputs (only roughly 40% of the quantity of gas necessary in surface gassing) can be used in this process as well. Further, a change of gassing between single or all segments and centre gassing (alternating gassing) and the combination of circulating and alternating gassing may be considered.

In circulating or alternating gassing, the gassing should take place over a period of time that is at least sufficient for a stationary state of flow to have developed in the reactor. However, the time intervals between switching from one to another gassing element should be small in comparison with the average residence time of the fluid phase in the reactor, so that solid matter deposits do not lead to a diminishing of the yield.

Retention of the biocatalysts is advantageously achieved by a circulation separator connected outside the reactor. The catalyst particles that leave the reactor with the fluid current are held back by sedimentation in the circulation separator and, under the effect of the circulation current, flow back into the reactor. The circulation current develops automatically as a result of the varying gas content in the reactor and in the circulation separator. Deflection elements and/or sieve plates are best incorporated in to the circulation separator in order to support circulation. A further possibility of generating a circulation current lies in additionally introducing a small amount of gas in the neighbourhood of the suspension outlet.

The circulation separator and its inflow and outflow pipes must be of such large dimensions that no solids can be deposited that lead to blocking. The distance h between the inlet and the outlet should be at least 0.5 m, so that disturbances to sedimentation by the inflowing stream are largely avoided.

One example of the embodiment of the invention is described in detail in the following with reference to the accompanying drawings, wherein:

DETAILED DESCRIPTION OF THE INVENTION

Figure 1:
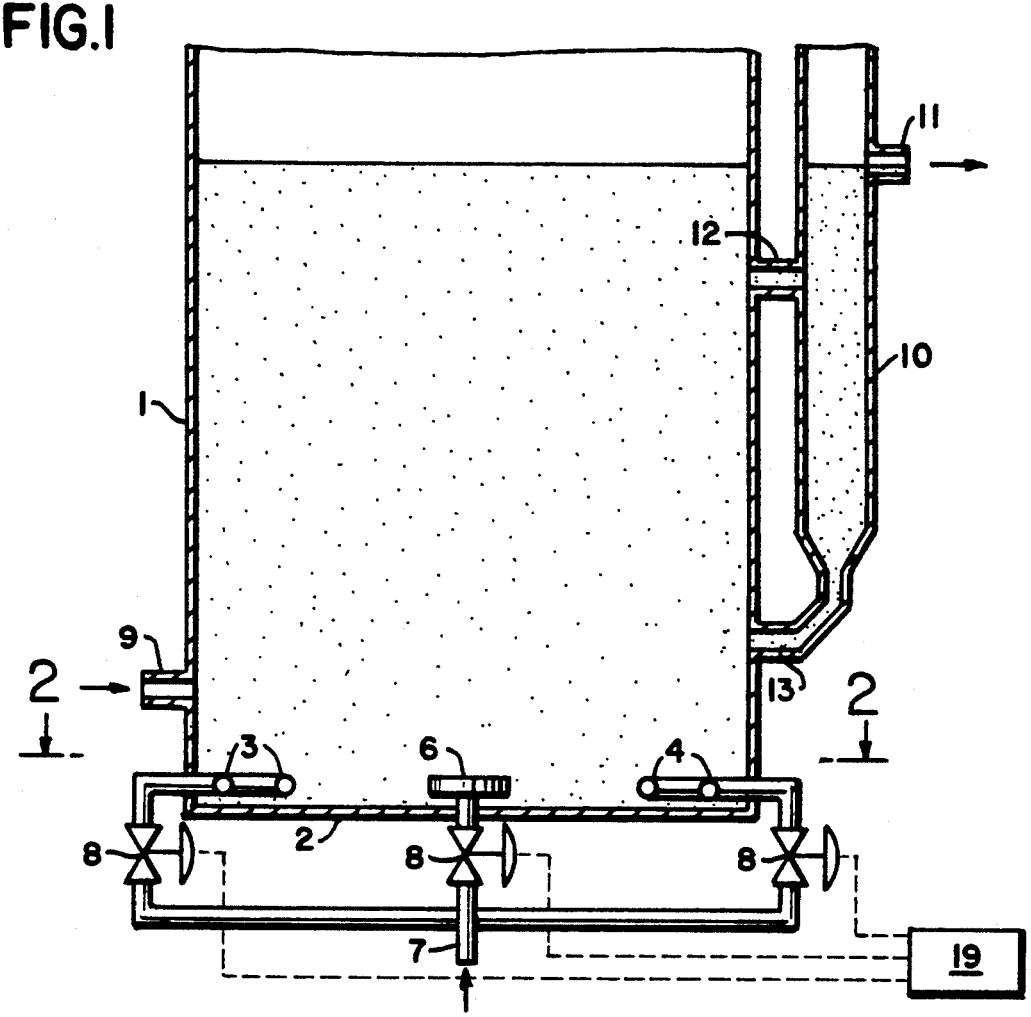
FIG. 1 is a schematic side view of the reactor with coupled circulation separator according to the invention.
Figure 2:
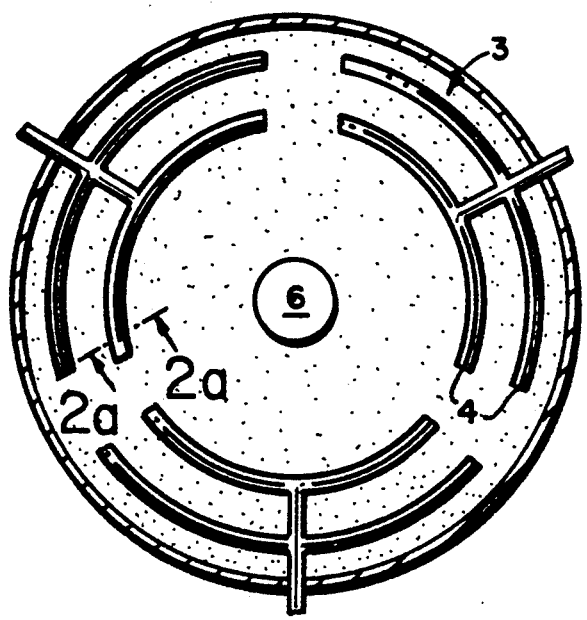
FIG. 2 is a cross section on the line A—A through the shown in FIG. 1 at the level of the gas distributor and FIG. 2a is a section along line X—X in FIG. 2.
Figure 2A:
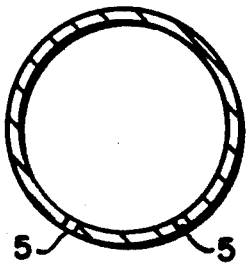
Figure 3:
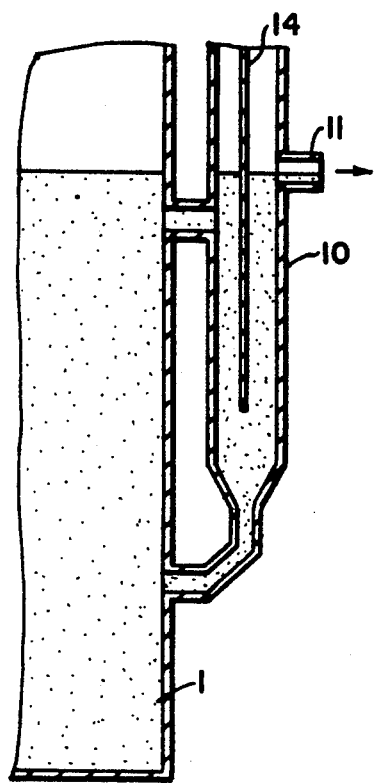
FIGS. 3 to 6 and 3a to 6a show various fittings in the circulation separator is their side and top views respectively.
Figure 4:
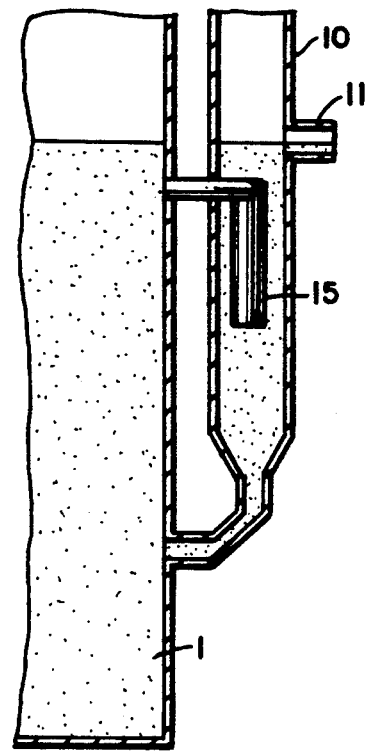
Figure 3A:
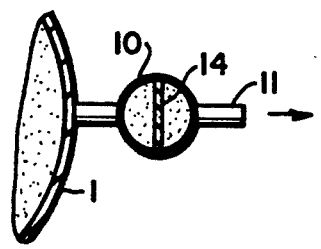
Figure 4A:
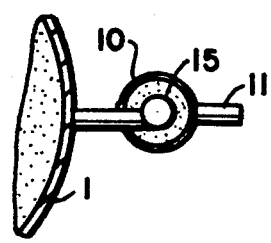
Figure 5:
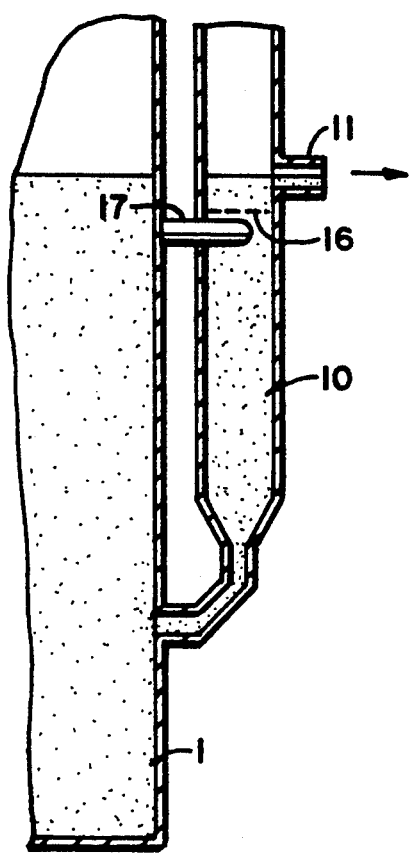
Figure 6:
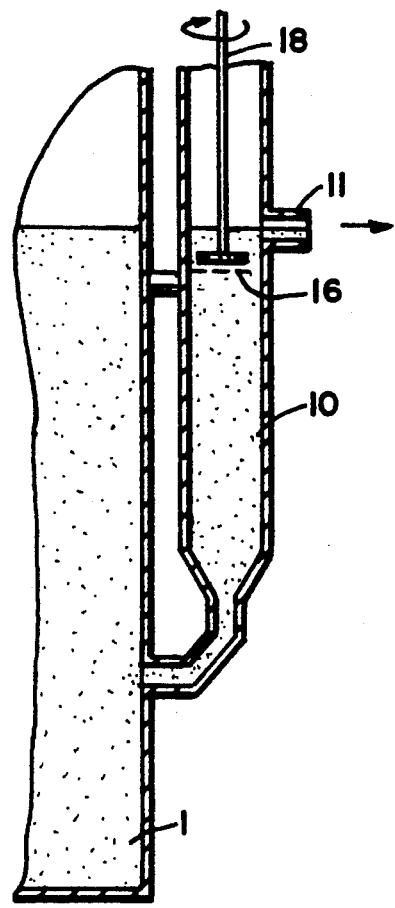
Figure 5A:
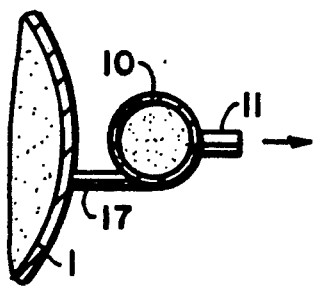
Figure 6A:
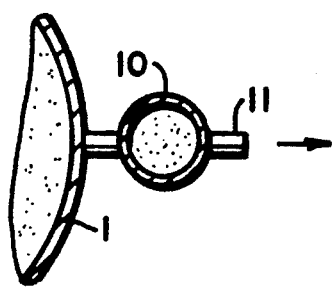

The reactor according to FIG. 1 and consists of a cylindrical container 1, 5 m in diameter and 5 m in height with a flat base 2. A gas distributor made up of three segments 3 with an angle α of 100° is arranged just above the container base 2. The gas distributor consists of two ring pipes 4 that are mounted at a distance of 25 cm from the container wall and 50 cm from each other. The pipes 4 have bores 5, 4 mm in diameter inclined downwards, and are separated by a distance of 25 cm. There is also a central gassing unit 6 in the middle.

Each gassing segment 3 or unit 6 may be controlled through a regulating valve 8 and is connected to the main gas pipe 7. The valves 8 are so controlled through a central regulating unit 19 that the fittings 3 and 6 receive gas one after the other so that a circulating or alternating gassing is produced.

In the reactor there is 30% by volume polyurethane foam flakes, which are covered with bacteria for effluent treatment. The average size of the particles is 4 mm and the density in the aqueous state is 1040 kg/m$^3$. By means of a gas quantity of 100 m$^3$/h, which corresponds to a specific power of roughly 14 watts/m$^3$ and an empty pipe gas velocity of 5 m/h, this biocatalyst is kept in motion, so that agglomeration of the particles and thus a reduction of the catalyst capacity is avoided. By this means, a continuous cleaning of problematical industrial effluents may be carried out by a continuous operation.

The effluent stream flowing into the reactor through the inlet 9, leaves the installation through the circulation separator 10 coupled to the bioreactor through the outlet 11. After the fine particles emanating from the production process of the catalyst have been discharged in the start-up phase of the biological cleaning process, the carrier material is retained in the interceptor by sedimentation. The interceptor has a diameter of only 500 mm for an effluent through put of 10 m$^3$/h. The length of the circulation separator between the inlet (12) and outlet (13) is roughly 2 m.

In cases where the overall height of the circulation separator has to be kept small because of the low height of the fluidized bed, the fittings shown in FIGS. 3 to 6 and 3a to 6a will be resorted to. As shown in FIGS. 3 and 4 3a and 4a, the distance between the position of the flow deflection in the separator and in the outlet will be increased by incorporation of a lee 14 or a stabilization zone 15, thus improving separation efficiency.

In embodiments shown in FIGS. 5 to 6 and 5a to 6a, the circulation separator 10 is additionally fitted with sieve plates 16. Such sieve plates 16 are especially suited for the retention of fine particles of the biocatalysts. However, this problem only arises if the particles greatly differ in size due to the production method or to abrasion in the reactor.

In order to prevent the sieve plates 16 from blocking up during operation, they are subjected to the effect of a tangentially opening fluid jet 17 or stirrer 18 is arranged above. Under the effect of the tangential jet (FIG. 5a) or the stirrers 18 (FIG. 6a) a spinning flow is generated, uniformally rinsing the sieve plates 16.

We claim:

1. A fluidized bed reactor for cultivating immobilized biocatalysts suspended in effluent, comprising:
    (a) a container for supporting a fluidized bed which includes a sidewall, a base forming a bottom, an inlet in the sidewall for effluent disposed above the base and an effluent outlet in the sidewall disposed above the base;
    (b) gas distributing means for gassing the fluidized bed which includes a plurality of spaced apart gas pipes within the container, each of said gas pipes having an inlet which is disposed through said container, and each of said gas pipes having a circular segment portion of a common annulus disposed parallel to the container base and having outflow openings for gas, and valve means disposed in each of said gas pipe inlets for controlling the flow of gas therethrough; and
    (c) a controlling unit coupled to each of the valve means for sequentially turning on and off each respective valve means one after the other to sequentially feed gas to the segment portions of the gas pipes to effect a sequential flow of gas from successive ones of the segment portions of the gas pipes, thereby to effect circulating gassing.

2. A fluidized bed reactor as claimed in claim 1, wherein the common annulus has a center, and wherein the gas distributing means further comprises a gas inlet at said center, a gas line for supplying gas to said central gas inlet and second valve means arranged in said gas line and coupled to said controlling unit for controlling the flow of gas to said central gas inlet.

3. A fluidized bed reactor as claimed in claim 2, wherein the controlling unit further comprises means for switching alternately between gassing through the central gas inlet and gassing through the segment portions of the gas pipes.

4. A fluidized bed reactor as claimed in claim 1, further comprising a retainer system for immobilized biocatalysts comprising a circulation separator connected to said outlet.

5. A fluidized bed reactor as claimed in claim 4, wherein the circulation separator includes deflection elements therein.

6. A fluidized bed reactor as claimed in claim 4, further comprising a second effluent inlet in the vicinity of the outlet.

7. A fluidized bed reactor according to claim 4, further comprising a tangential opening in the separator for the tangential introduction of a suspension.

8. A fluidized bed reactor according to claim 4, wherein the circulation separator includes sieve plates therein.

* * * * *